United States Patent
Jang et al.

(10) Patent No.: US 9,245,740 B2
(45) Date of Patent: Jan. 26, 2016

(54) AMINO-SILYL AMINE COMPOUND, METHOD FOR PREPARING THE SAME AND SILICON-CONTAINING THIN-FILM USING THE SAME

(71) Applicant: DNF Co., Ltd., Daejeon (KR)

(72) Inventors: Se Jin Jang, Daegu (KR); Sang Do Lee, Daejeon (KR); Sung Gi Kim, Daejeon (KR); Jong Hyun Kim, Daejeon (KR); Byeong Il Yang, Daejeon (KR); Jang Hyeon Seok, Daejeon (KR); Sang Ick Lee, Daejeon (KR); Myong Woon Kim, Daejeon (KR)

(73) Assignee: DNF Co., Ltd., Daejeon (KR)

( * ) Notice: Subject to any disclaimer, the term of this patent is extended or adjusted under 35 U.S.C. 154(b) by 0 days.

(21) Appl. No.: 14/296,270

(22) Filed: Jun. 4, 2014

(65) Prior Publication Data
US 2014/0363985 A1 Dec. 11, 2014

(30) Foreign Application Priority Data

Jun. 7, 2013 (KR) .................. 10-2013-0065323
Dec. 19, 2013 (KR) .................. 10-2013-0159638

(51) Int. Cl.
| | |
|---|---|
| C07F 7/02 | (2006.01) |
| H01L 21/02 | (2006.01) |
| C07F 7/10 | (2006.01) |
| C23C 16/34 | (2006.01) |
| C23C 16/455 | (2006.01) |

(52) U.S. Cl.
CPC ............ *H01L 21/02167* (2013.01); *C07F 7/10* (2013.01); *C23C 16/345* (2013.01); *C23C 16/347* (2013.01); *C23C 16/45553* (2013.01); *H01L 21/0217* (2013.01); *H01L 21/0228* (2013.01); *H01L 21/02164* (2013.01); *H01L 21/02219* (2013.01); *H01L 21/02274* (2013.01)

(58) Field of Classification Search
CPC ........................... C23C 16/345; H01L 21/022
USPC ........................................... 556/412; 438/786
See application file for complete search history.

(56) References Cited

U.S. PATENT DOCUMENTS 6,391,803 B1 * 5/2002 Kim ...................... C23C 16/345
                                                            257/E21.271

FOREIGN PATENT DOCUMENTS

| KR | 1020070055898 A | 5/2007 |
|---|---|---|
| TW | 200610057 | 4/2006 |

OTHER PUBLICATIONS

Breed, L.W. et al., "Functionally substituted trisilylamine derivatives", Journal of Organometallic Chemistry, (1968), 447-457, vol. 11.
Wannagat, U. et al., "Zur Umsetzung von metallierten (Di) Alkylaminosilylaminen mit Chlorsilanen.", Monatshefte für Chemie/Chemical Monthly, (1968),1376-1382, vol. 99. English-language Abstract.

* cited by examiner

*Primary Examiner* — Porfirio Nazario Gonzalez
*Assistant Examiner* — Kofi Adzamli
(74) *Attorney, Agent, or Firm* — The Webb Law Firm

(57) ABSTRACT

Provided are a novel amino-silyl amine compound, a method for preparing the same, and a silicon-containing thin-film using the same, wherein the amino-silyl amine compound has thermal stability and high volatility and is maintained in a liquid state at room temperature and under a pressure where handling is easy to thereby form a silicon-containing thin-film having high purity and excellent physical and electrical properties by various deposition methods.

3 Claims, 15 Drawing Sheets

FIG. 12

| | bis(dimethylaminomethylsilyl) trimethylsilyl amine thickness (Å) | | | |
|---|---|---|---|---|
| | 60/10/0 (N2/NH3/Ar) | 200/30/0 (N2/NH3/Ar) | 0/50/30 (N2/NH3/Ar) | 0/0/50 (N2/NH3/Ar) |
| Before (Å) | 792.4 | 281.9 | 453.3 | 2976.9 |
| After (Å) | 739.1 | 276.2 | 327.6 | 2953.8 |

AMINO-SILYL AMINE COMPOUND, METHOD FOR PREPARING THE SAME AND SILICON-CONTAINING THIN-FILM USING THE SAME

CROSS-REFERENCE TO RELATED APPLICATIONS

This application claims priority to Korean Patent Application Nos. 10-2013-0065323 and 10-2013-0159638, filed Jun. 7, 2013 and Dec. 19, 2013, respectively, the disclosures of which are hereby incorporated in their entirety by reference.

TECHNICAL FIELD

The present invention relates to a novel amino-silyl amine compound, a method for preparing the same, and a silicon-containing thin-film using the same, and more particularly, to a novel amino-silyl amine compound having thermal stability and high volatility and being maintained in a liquid state at room temperature and under a pressure where handling is easy, a method for preparing the same, and a silicon-containing thin-film using the same.

BACKGROUND

A silicon-containing thin-film is manufactured in various shapes, including silicon, silicon oxide, silicon nitride, silicon carbonitride, silicon oxynitride, and the like, by various deposition processes in a semiconductor field, and the application field is wide.

In particular, silicon oxide and silicon nitride function as an insulating film, a diffusion prevention film, a hard mask, an etching stop layer, a seed layer, a spacer, trench isolation, intermetallic dielectric material and a protective layer in manufacturing a semiconductor device, due to significantly excellent block property and oxidation resistance.

Recently, polycrystalline silicon thin-film has been used to a thin-film transistor (TFT), a solar cell, and the like, and the application field becomes various.

As a representative technology known for manufacturing a silicon-containing thin-film, there are metal organic chemical vapor deposition (MOCVD) forming a film on a surface of a substrate by reacting a silicon precursor in a mixed gas form and a reactive gas, or forming a film by direct reaction on a surface, and atomic layer deposition (ALD) forming a film by physical or chemical adsorption of a silicon precursor in a gas form on a surface of a substrate, followed by sequential introduction of a reactive gas. In addition, various technologies for manufacturing a thin-film such as low pressure chemical vapor deposition (LPCVD) using the method, plasma enhanced chemical vapor deposition (PECVD), plasma enhanced atomic layer deposition (PEALD) using plasma capable of being deposited at a low temperature, and the like, are applied to next-generation semiconductor and a display device manufacturing process, thereby being used to form ultra-fine patterns and deposit ultra-thin-film having uniform and excellent properties in nano-sized thickness.

Representative examples of a precursor used in forming a silicon-containing thin-film as described in Korean Patent Laid-Open Publication No. KR 2007-0055898 include silanes, silane chlorides, amino silanes and alkoxysilanes, and more specifically, silane chlorides such as dichlorosilane ($SiH_2Cl_2$) and hexachlorodisilane ($Cl_3SiSiCl_3$) and trisilylamine ($N(SiH_3)_3$)), bis-diethylaminosilane ($H_2Si(N(CH_2CH_2)_2)_2$)) and di-isopropylaminosilane ($H_3SiN(i-C_3H_7)_2$)), and the like, and used in a mass production of a semiconductor and a display.

However, a technology of forming a ultra-fine thin-film having a uniform and thin thickness and excellent electrical properties at a desired low temperature according to miniaturization of devices caused by ultra high integration of the devices, an increase in an aspect ratio, and diversification of device material has been demanded, and thus, high temperature process at 600° C. or more, step coverage, etching property, and physical and electrical properties of a thin-film at the time of using the existing silicon precursor are emerging as an issue, and accordingly, excellent novel silicon precursor has been demanded to be developed.

RELATED ART DOCUMENT (Patent Document 1) Korean Patent Laid-Open Publication No. KR 2007-0055898

SUMMARY

An embodiment of the present invention is directed to providing a novel amino-silyl amine compound.

Another embodiment of the present invention is directed to providing a novel amino-silyl amine compound which is a precursor compound for thin-film deposition.

Another embodiment of the present invention is directed to providing a method for preparing an amino-silyl amine compound.

Another embodiment of the present invention is directed to providing a silicon-containing composition for thin-film deposition containing the amino-silyl amine compound of the present invention, a method for manufacturing a thin-film using the same, and a silicon-containing thin-film manufactured by containing the amino-silyl amine compound of the present invention.

In one general aspect, the present invention provides a novel amino-silyl amine compound capable of forming a silicon thin-film having excellent cohesion, high deposition rate, and superior physical and electrical properties even at a low temperature.

The novel amino-silyl amine compound of the present invention is represented by the following Chemical Formula 1:

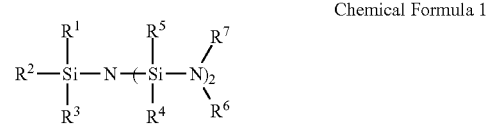

Chemical Formula 1 in Chemical Formula 1, $R^1$ to $R^5$ are each independently hydrogen, halogen, (C1-C7)alkyl, (C2-C7)alkenyl, (C2-C7)alkynyl, (C3-C7)cycloalkyl or (C6-C12)aryl;

$R^6$ and $R^7$ are each independently hydrogen, (C1-C7)alkyl, (C2-C7)alkenyl, (C2-C7)alkynyl, (C3-C10)cycloalkyl or (C6-C12)aryl, provided that a case where all $R^1$ to $R^7$ are methyl is excluded; and the alkyl, alkenyl, alkynyl, cycloalkyl, and aryl of $R^1$ to $R^5$, and the alkyl, alkenyl, alkynyl, cycloalkyl, and aryl of $R^6$ and $R^7$ may be further substituted with halogen, (C1-C7)alkyl, (C1-C7)alkoxy, or (C1-C7)aryloxy.

In the Chemical Formula 1 above representing the amino-silyl amine compound of the present invention, the amino-silyl amine compound where all R¹ to R⁷ are methyl is solid at room temperature and under atmospheric pressure, whereas the amino-silyl amine compound of the present invention is maintained in liquid state to have high volatility, thereby being easy to form a thin-film.

In addition, due to $Si_3N$ trigonal planar molecular structure having three silicon atoms bonded to central nitrogen atom, the amino-silyl amine compound of the present invention has high thermal stability and low activation energy to thereby have excellent reactivity, and does not produce non-volatile by-product to be capable of easily forming a silicon-containing thin-film having high purity.

In order for the amino-silyl amine compound represented by the Chemical Formula 1 above according to an exemplary embodiment of the present invention to form a thin-film having high thermal stability and reactivity, and high purity, it is preferred that in the Chemical Formula 1 above, $R^1$ to $R^5$ may be each independently hydrogen, halogen, (C1-C5)alkyl, (C2-C5)alkenyl, (C2-C5)alkynyl, (C3-C6)cycloalkyl or (C6-C10)aryl; and $R^6$ and $R^7$ may be each independently hydrogen, (C1-C5)alkyl, (C2-C5)alkenyl, (C2-C5)alkynyl, (C3-C5)cycloalkyl or (C6-C10)aryl, provided that a case where all $R^1$ to $R^7$ are methyl is excluded.

More preferably, in the Chemical Formula 1 above, $R^1$ to $R^5$ may be each independently hydrogen or (C1-C5)alkyl; and $R^6$ and $R^7$ may be each independently hydrogen or (C1-C5)alkyl, provided that a case where all $R^1$ to $R^7$ are methyl is excluded.

The Chemical Formula 1 may be selected from the following compounds, but the present invention is not limited thereto:

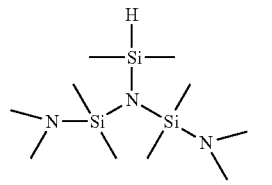 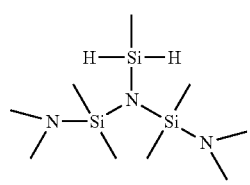

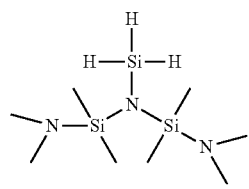 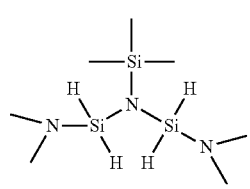

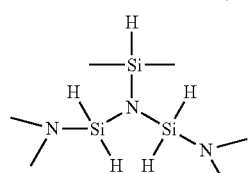 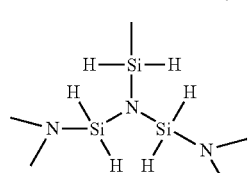

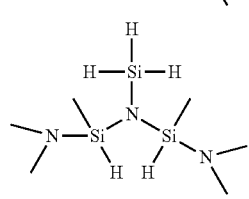 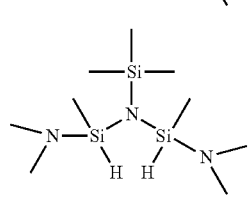

-continued

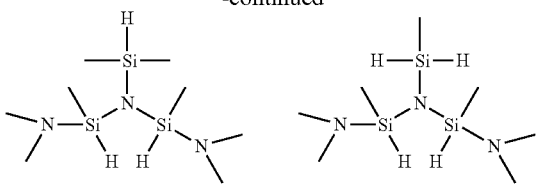 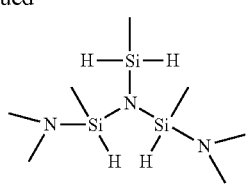

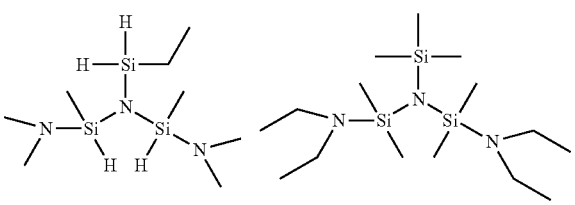 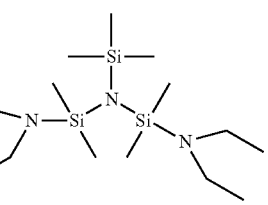

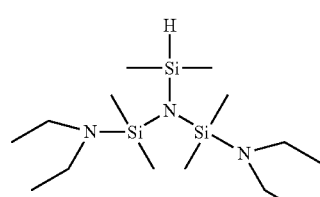

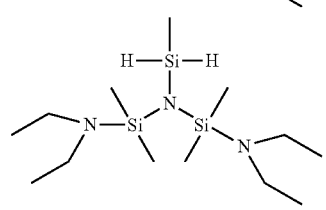

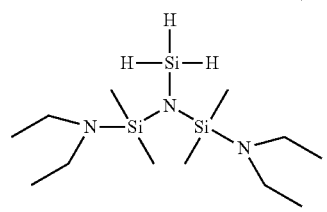

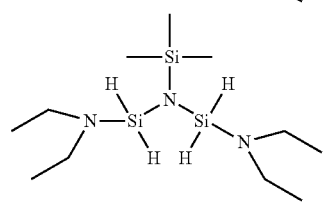

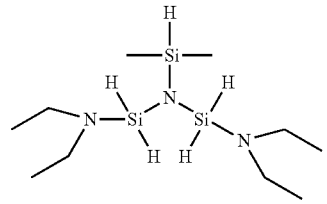

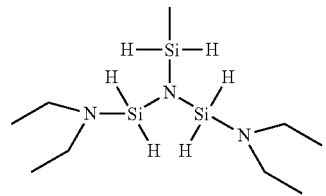

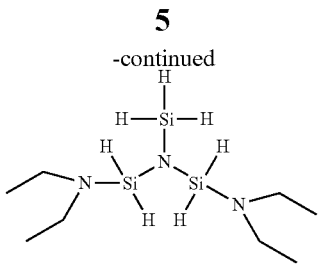
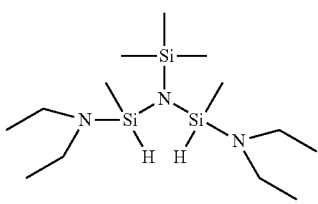
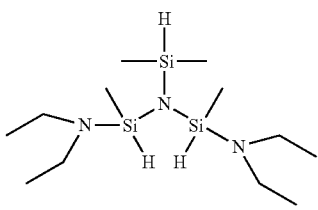
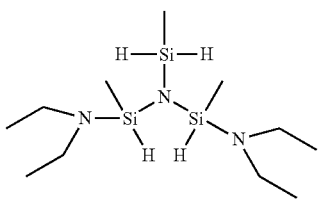
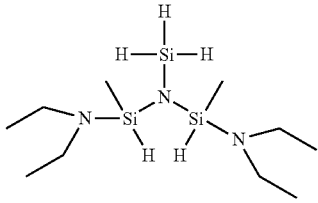
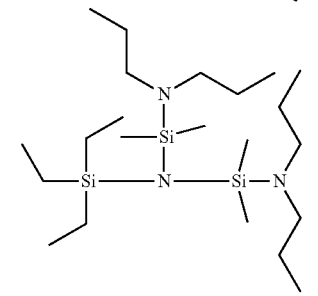
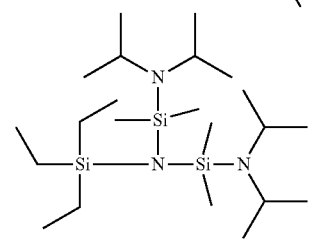

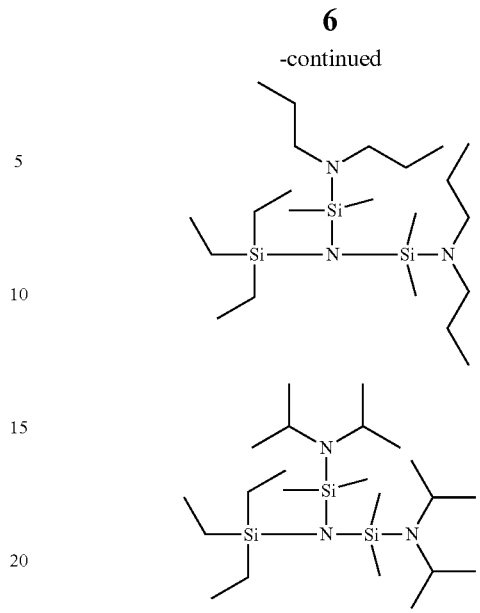

The term: "alkyl", "alkoxy", and other substituents including "alkyl" part described in the present invention may include all linear or branched types. In addition, "aryl" described in the present invention, which is an organic radical derived from aromatic hydrocarbon by removal of one hydrogen, may include single or fused ring system including ring atoms of 4 to 7 in each ring, preferably, 5 or 6, and may include a plurality of aryls linked with a single bond. Specific examples of aryl may include phenyl, naphthyl, biphenyl, anthryl, indenyl, fluorenyl, and the like, but the present invention is not limited thereto. Further, "alkenyl" of the present invention, which is linear or branched hydrocarbon including at least one double bond, may include vinyl, prop-1-en, buta-1,3-diene, and the like, but the present invention is not limited thereto, and "alkynyl" of the present invention may include linear or branched hydrocarbon including at least one triple bond.

The amino-silyl amine compound represented by the Chemical Formula 1 above of the present invention may be preferably a silicon-containing precursor compound for thin-film deposition.

In another general aspect, the present invention provides a method for preparing the amino-silyl amine compound represented by the Chemical Formula 1 above, the method including: preparing the compound represented by the Chemical Formula 1 above by reacting a compound represented by the following Chemical Formula 3 with a compound represented by the following Chemical Formula 4 in the presence of a base represented by the following Chemical Formula 2 or (C1-C7)alkyllithium, Chemical Formula 2

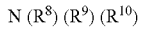

Chemical Formula 3

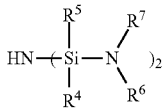

-continued

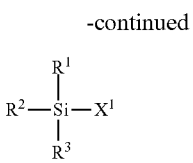

Chemical Formula 4 in Chemical Formulas 1 to 4, $R^8$ to $R^{10}$ are each independently (C1-C7)alkyl;

$R^1$ to $R^5$ are each independently hydrogen, halogen, (C1-C7)alkyl, (C2-C7)alkenyl, (C2-C7)alkynyl, (C3-C7)cycloalkyl or (C6-C12)aryl;

$R^6$ and $R^7$ are each independently hydrogen, (C1-C7)alkyl, (C2-C7)alkenyl, (C2-C7)alkynyl, (C3-C10)cycloalkyl or (C6-C12)aryl, provided that a case where all $R^1$ to $R^7$ are methyl is excluded;

the alkyl, alkenyl, alkynyl, cycloalkyl, and aryl of $R^1$ to $R^5$, and the alkyl, alkenyl, alkynyl, cycloalkyl, and aryl of $R^6$ and $R^7$ may be further substituted with halogen, (C1-C7)alkyl, (C1-C7)alkoxy, or (C1-C7)aryloxy; and $X^1$ is halogen.

(C1-C7) alkyl lithium according an exemplary embodiment of the present invention is compound where lithium is bonded to alkyl having carbon atoms of 1 to 7 for example, methyl lithium, n-butyl lithium, and the like, and preferably, n-butyl lithium.

The method may further include:

preparing a compound represented by the following Chemical Formula 14 by reacting a compound represented by the following Chemical Formula 12 with a compound represented by the following Chemical Formula 13 in the presence of a compound represented by the following Chemical Formula 11; and preparing the compound represented by the Chemical Formula 3 above by reacting the compound represented by the following Chemical Formula 14 with a compound represented by the following Chemical Formula 15:

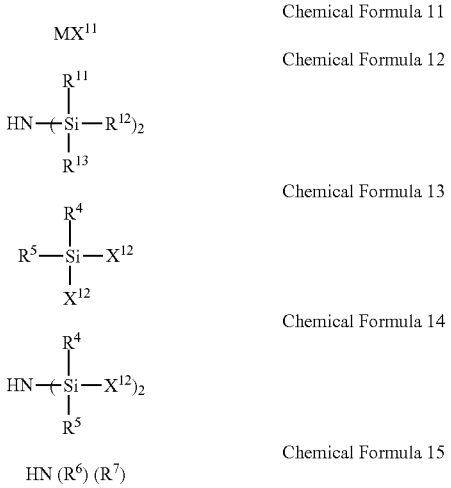

in Chemical Formula 11 to 15,

M is B, Al or Sn;

$R^{11}$ to $R^{13}$ are each independently (C1-C7)alkyl;

$R^4$ and $R^5$ are each independently hydrogen, halogen, (C1-C7)alkyl, (C2-C7)alkenyl, (C2-C7)alkynyl, (C3-C7)cycloalkyl, or (C6-C12)aryl;

$R^6$ and $R^7$ are each independently hydrogen, (C1-C7)alkyl, (C2-C7)alkenyl, (C2-C7)alkynyl, (C3-C10)cycloalkyl or (C6-C12)aryl; and $X^{11}$ and $X^{12}$ are each independently halogen.

The Chemical Formula 11 according to an exemplary embodiment of the present invention is a halogenated metal, wherein the metal is B, Al or Sn, preferably, Al.

The solvent used in the preparing method of the present invention is not limited if a solvent, among general organic solvents, is not reacted with the starting material, for example, may be at least one kind selected from a group consisting of normal hexane (n-hexane), cyclohexane, normal pentane (n-pentane), diethyl ether, toluene, tetrahydrofuran (THF), dichloromethane (DCM), and trichloromethane (chloroform).

The reaction temperature in the preparing method of the present invention is not limited if the temperature is used in general organic synthesis; however, may be varied depending on the reaction time, the reaction material, and an amount of the starting material, wherein the reaction needs to be finished after confirming that the starting material is completely consumed by NMR, GC, and the like. When the reaction is finished, a solvent may be removed by filtration, followed by simple distillation, under reduced pressure, to thereby separate and refine a desired material by general methods such as fractional distillation, distillation under reduced pressure, and the like.

In another general aspect, the present invention provides a silicon-containing composition for thin-film deposition including the amino-silyl amine compound as described above, and a method for manufacturing a silicon-containing thin-film including the same.

The silicon-containing composition for thin-film deposition may contain the amino-silyl amine compound as a precursor for thin-film deposition, and the amino-silyl amine compound in the composition may have a content within the range recognized by a person skilled in the art in consideration of film forming conditions, or thickness, properties, and the like, of the thin-film.

In another general aspect, the present invention provides a silicon-containing thin-film manufactured by containing the amino-silyl amine compound as described above.

The silicon-containing thin-film of the present invention may be manufactured by general methods, for example, metal organic chemical vapor deposition (MOCVD), atomic layer deposition (ALD), low pressure chemical vapor deposition (LPCVD), plasma enhanced chemical vapor deposition (PECVD), plasma enhanced atomic layer deposition (PEALD), and the like.

The amino-silyl amine compound of the present invention has low activation energy, high reactivity and little non-volatile by-products, such that the silicon-containing thin-film manufactured by using the amino-silyl amine compound as a precursor may have high purity and excellent physical and electrical properties.

BRIEF DESCRIPTION OF THE DRAWINGS

The above and other objects, features and advantages of the present invention will become apparent from the following description of preferred embodiments given in conjunction with the accompanying drawings, in which:

FIG. 12 shows a thickness of the silicon-containing thin-film manufactured by Example 10 through TEM;

DETAILED DESCRIPTION OF EMBODIMENTS

Figure 1:
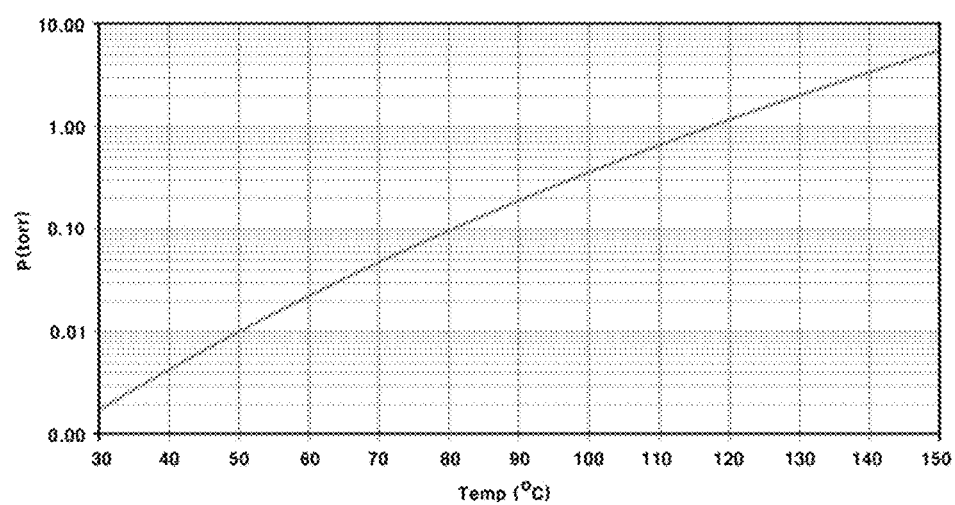
FIG. 1 shows a result obtained by measuring vapor pressure of alkylaminosilane prepared by Example 3.
Figure 2:
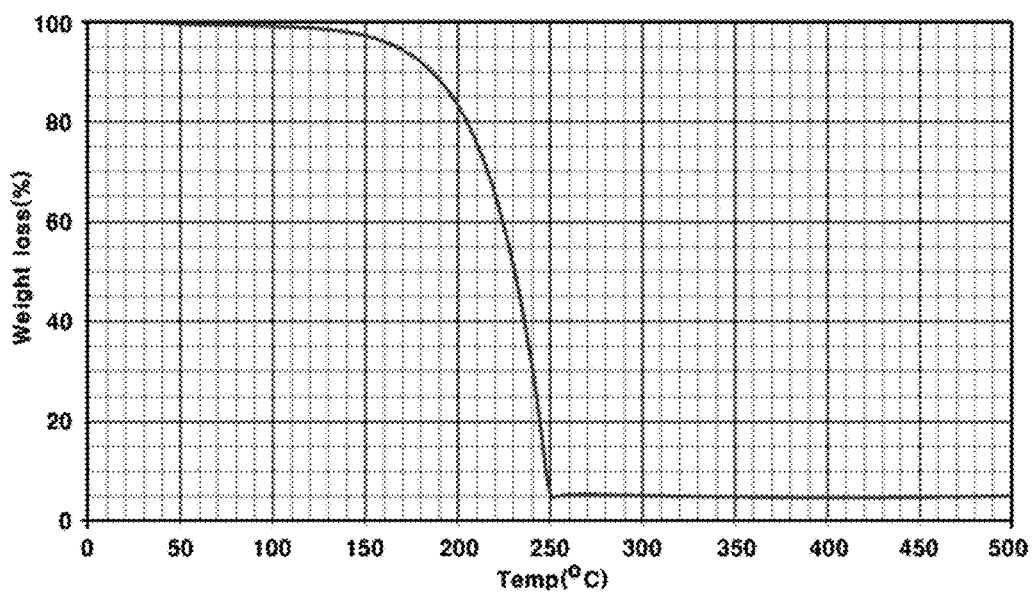
FIG. 2 shows a result obtained by analyzing thermogravimetry of alkylaminosilane prepared by Example 4.
Figure 3:
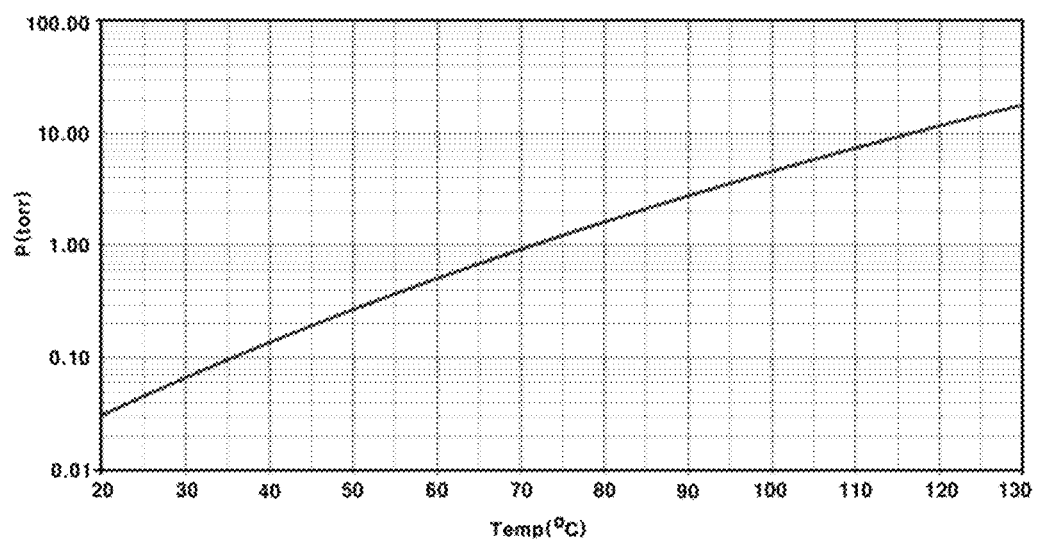
FIG. 3 shows a result obtained by measuring vapor pressure of alkylaminosilane prepared by Example 4.
Figure 4:
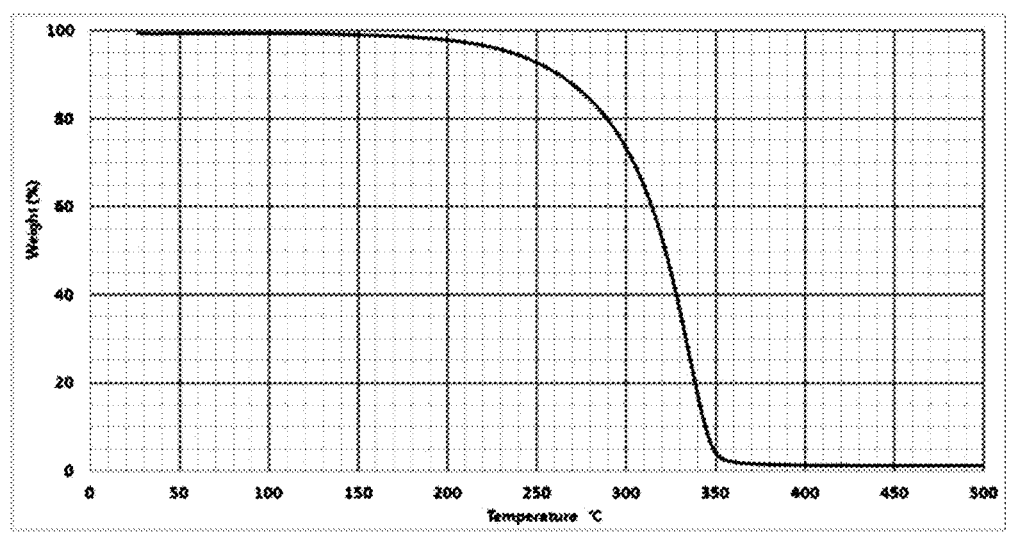
FIG. 4 shows a result obtained by analyzing thermogravimetry of alkylaminosilane prepared by Examples 5 and 6.
Figure 5:
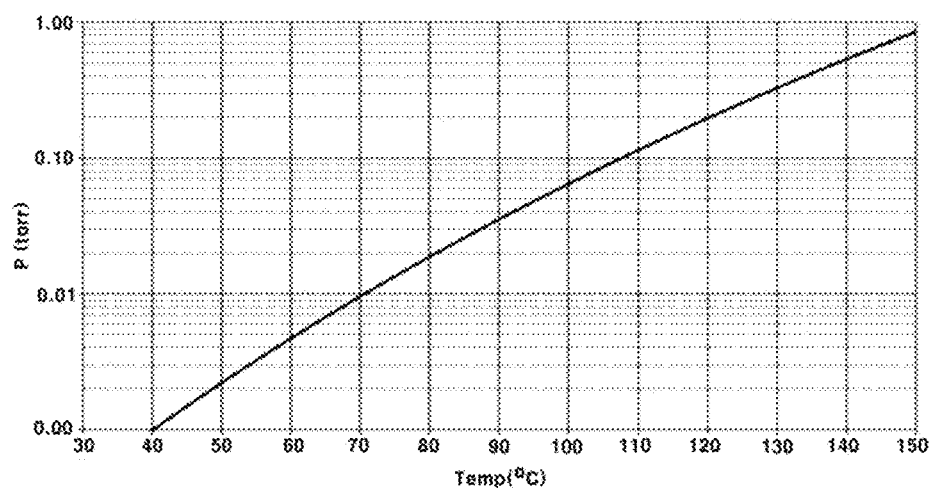
FIG. 5 shows a result obtained by measuring vapor pressure of alkylaminosilane prepared by Examples 5 and 6.
Figure 6:
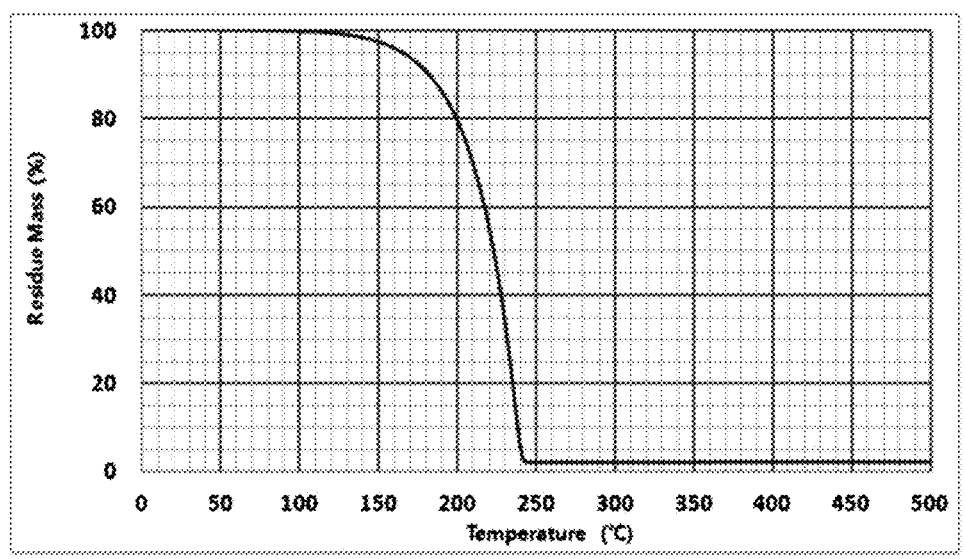
FIG. 6 shows a result obtained by analyzing thermogravimetry of alkylaminosilane prepared by Example 8.
Figure 7:
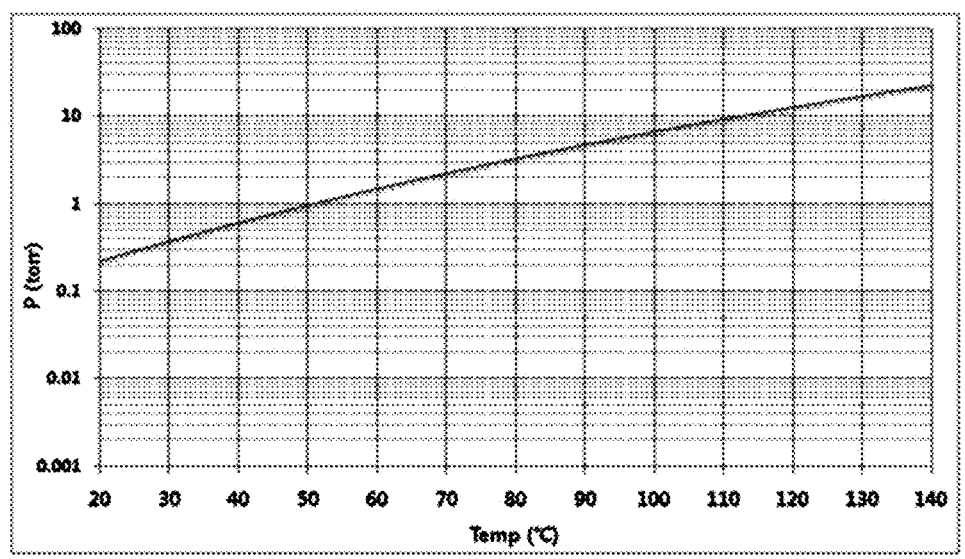
FIG. 7 shows a result obtained by measuring vapor pressure of alkylaminosilane prepared by Example 8.

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, the present invention will be described in more detail with reference to the following exemplary embodiments. However, the following exemplary embodiments describe the present invention by way of example only but are not limited thereto.

The following Examples of all compounds were practiced under anhydrous and inert atmosphere using a glovebox or a Schlenk pipe, products were analyzed by $^1$H Nuclear Magnetic Resonance (NMR), thermogravimetric analysis (TGA) and gas chromatography (GC), each thickness of deposited thin-films were measured by Ellipsometer and Transmission Electron Microscope (TEM), and components of the deposited films were analyzed by infrared spectroscopy and Auger Electron Spectroscopy (AES).

Example 1

Synthesis of Diethylamino Dimethyl Disilazane 250 g (1.55 mol) of hexamethyldisilazane ((($CH_3)_3Si)_2$NH) and 10 g (0.075 mol) of aluminum chloride ($AlCl_3$) were put into 2000 mL of a flame-dried Schlenk flask under anhydrous and inert atmosphere while stirring, 499.80 g (3.87 mol) of dichloro dimethylsilane (($CH_3)_2SiCl_2$) was slowly added thereto while maintaining temperature of 25° C. and a temperature of the reaction solution was slowly raised to 40° C. The mixed reaction solution was stirred for 3 hours and the produced chlorotrimethylsilane (($CH_3)_3SiCl$) and the excessively added dichloro dimethylsilane (($CH_3)_2SiCl_2$) were removed therefrom by simple distillation or distillation under reduced pressure. The recovered chloro dimethyl disilazane ((($CH_3)_2SiCl)_2NH$)) solution was stirred and then 475.45 g (6.5 mol) of diethylamine (($CH_3CH_2)_2NH$) was slowly added thereto while maintaining temperature of −15° C. After the addition was completed, a temperature of the reaction solution was slowly raised to room temperature, and the reaction solution was stirred at room temperature for 6 hours. After the white solid obtained by filtration was removed to obtain a filtrate, solvent was removed from the filtrate under reduced pressure, and 319.90 g (1.16 mol) of diethylamino dimethyl disilazane (($CH_3)_2SiN(CH_2CH_3)_2)_2NH$) was obtained by reduced pressure distillation with a yield of 75%.

$^1$H NMR (in $C_6D_6$) δ 0.14 (s, 12H, HNSi($CH_3)_2$N), 0.97 (t, 12H, Si(NCH$_2$CH$_3$)$_2$), 3.42 (q, 8H, Si(NCH$_2$CH$_3$)$_2$), Boiling Point 238° C.

Example 2

Synthesis of Diethylamino Dimethyl Disilazane 250 g (1.55 mol) of hexamethyldisilazane ((($CH_3)_3Si)_2$NH) and 10 g (0.075 mol) of aluminum chloride ($AlCl_3$) were put into 2000 mL of a flame-dried Schlenk flask under anhydrous and inert atmosphere while stirring, 499.80 g (3.87 mol) of dichloro dimethylsilane (($CH_3)_2SiCl_2$) was slowly added thereto while maintaining temperature of 25° C., and a temperature of the reaction solution was slowly raised to 40° C. The mixed reaction solution was stirred for 3 hours and the produced chlorotrimethylsilane (($CH_3)_3SiCl$) and the excessively added dichloro dimethylsilane (($CH_3)_2SiCl_2$) were removed therefrom by simple distillation or distillation under reduced pressure. The recovered chloro dimethyl disilazane ((($CH_3)_2SiCl)_2NH$)) solution was stirred and then 168.52 g (4.2 mol) of dimethylamine (($CH_3)_2NH$) was slowly added thereto while maintaining temperature of −15° C. After the addition was completed, a temperature of the reaction solution was slowly raised to room temperature, and the reaction solution was stirred at room temperature for 6 hours. The white solid obtained by filtration was removed to obtain a filtrate. Solvent was removed from the filtrate under reduced pressure, and 146.51 g (0.74 mol) of dimethylamino dimethyl disilazane (($CH_3SiHN(CH_3)_2)_2NH$) was obtained by reduced pressure distillation with a yield of 75%.

$^1$H-NMR (in $C_6D_6$) δ 0.09 (s, 12H, ((($CH_3)_2)_2N(CH_3)_2Si)_2$NH), 2.45 (s, 12H, ((($CH_3)_2)_2N(CH_3)_2Si)_2NH$).

Example 3

Synthesis of Bis-Diethylamino Dimethylsilyl Trimethylsilyl Amine 180 g (0.65 mol) of diethylamino dimethyl disilazane (($CH_3$)$_2$SiN($CH_2CH_3$)$_2$)$_2$NH) synthesized by Example 1 above and 200 ml of n-hexane organic solvent were added to 2000 mL of a flame-dried flask under anhydrous and inert atmosphere while stirring, and 202.16 g (0.65 mol) of 2.29M normal butyl lithium (n-$C_4H_9$Li).hexane ($C_6H_{14}$) solution was slowly added while maintaining a temperature of −15° C. After the addition was completed, a temperature of the reaction solution was slowly raised to room temperature, and the reaction solution was stirred for 12 hours and 200 ml of tetrahydrofuran (O($C_2H_2$)$_2$) was added thereto. 70.94 g (0.65 mol) of chlorotrimethylsilane was slowly added to the reaction solution while maintaining a temperature of −20° C. After the addition was completed, a temperature of the reaction solution was slowly raised to 65° C. and the reaction solution was stirred for 12 hours while maintaining the temperature. After the reaction was completed, the white solid obtained by filtration of the reaction mixture was removed to obtain a filtrate, solvent was removed from the filtrate under reduced pressure, and 159 g (0.46 mol) of bis-diethylamino dimethylsilyl trimethylsilyl amine (($CH_3$)$_3$SiN(Si($CH_3$)$_2$N($CH_2CH_3$)$_2$)$_2$) was obtained by reduced pressure distillation with a yield of 70%.

$^1$H-NMR (in$C_6D_6$) δ 0.30 (s, 12H, NSi($CH_3$)$_2$N), 0.32 (s, 9H, Si($CH_3$)$_3$), 0.99 (t, 12H, Si(N$CH_2CH_3$)$_2$), 2.82 (q, 8H, Si(N$CH_2$$CH_3$)$_2$); Boiling Point 279° C.; GC Analysis Result >99.85%.

Example 4

Synthesis of Bis-Dimethylaminodimethylsilyl Dimethylsilyl Amine 140 g (0.64 mol) of dimethylamino dimethyl disilazane (($CH_3$)$_2$SiN($CH_3$)$_2$)$_2$NH) synthesized by Example 2 above and 200 ml of n-hexane organic solvent were added to 2000 mL of a flame-dried flask under anhydrous and inert atmosphere while stirring, and 185.74 g (0.64 mol) of 2.29M normal butyl lithium (n-$C_4H_9$Li).hexane ($C_6H_{14}$) solution was slowly added while maintaining a temperature of −15° C. After the addition was completed, a temperature of the reaction solution was slowly raised to room temperature, and the reaction solution was stirred for 12 hours and 200 ml of tetrahydrofuran (O($C_2H_2$)$_2$) was added thereto. 60.36 g (0.64 mol) of chlorodimethylsilane was slowly added to the reaction solution while maintaining a temperature of −20° C. After the addition was completed, a temperature of the reaction solution was slowly raised to 65° C. and the reaction solution was stirred for 12 hours while maintaining the temperature. After the white solid obtained by filtration was removed to obtain a filtrate, solvent was removed from the filtrate under reduced pressure, and 123.96 g (0.45 mol) of bis-dimethylaminodimethylsilyl dimethylsilyl amine ((($CH_3$)$_2$)$_2$N($CH_3$)$_2$Si)$_2$NSiH($CH_3$)$_2$) was obtained by reduced pressure distillation with a yield of 65%.

$^1$H-NMR (in$C_6D_6$) δ 0.21 (s, 12H, (($CH_3$)$_2$)$_2$N($CH_3$)$_2$Si)$_2$N), 0.30 (d, 6H, NSiH($CH_3$)$_2$), 2.41 (t, 12H, (($CH_3$)$_2$)$_2$N($CH_3$)$_2$Si)$_2$N), 4.61 (m, 1H, NSiH($CH_3$)$_2$); Boiling Point 229° C.; GC Analysis Result >99.39%.

Example 5

Synthesis of Tris-Diethylaminodimethylsilyl Amine 180 g (0.65 mol) of diethylamino dimethyl disilazane (($CH_3$)$_2$SiN($CH_2CH_3$)$_2$)$_2$NH) synthesized by Example 1 above and 200 ml of n-hexane organic solvent were added to 2000 mL of a flame-dried flask under anhydrous and inert atmosphere while stirring, and 202.16 g (0.65 mol) of 2.29M normal butyl lithium (n-$C_4H_9$Li).hexane ($C_6H_{14}$) solution was slowly added while maintaining a temperature of −15° C. After the addition was completed, a temperature of the reaction solution was slowly raised to room temperature, and the reaction solution was stirred for 12 hours and 200 ml of tetrahydrofuran (O($C_2H_2$)$_2$) was added thereto. 108.25 g (0.65 mol) of chloro-dimethyl diethylaminosilane (($CH_3CH_2$)$_2$NSiCl($CH_3$)$_2$) synthesized by reacting dichloro dimethylsilane ($Cl_2$Si($CH_3$)$_2$) with 2 equivalents of diethylamine in a quantitative scheme was slowly added to the reaction solution while maintaining a temperature of −20° C. After the addition was completed, a temperature of the reaction solution was slowly raised to 65° C. and the reaction solution was stirred for 12 hours while maintaining the temperature. After the reaction was completed, the white solid obtained by filtration of the reaction mixture was removed to obtain a filtrate. Solvent was removed from the filtrate under reduced pressure, and 119.00 g (0.29 mol) of tris-diethylaminosilyl amine (N(Si($CH_3$)$_2$N($CH_2CH_3$)$_2$)$_3$) was obtained by reduced pressure distillation with a yield of 45%.

$^1$H NMR (in$C_6D_6$) δ 0.37 (s, 18H, NSi($CH_3$)$_2$N), 1.02 (t, 18H, Si(N$CH_2CH_3$)$_2$), 2.86 (q, 12H, Si(N$CH_2$$CH_3$)$_2$); Boiling Point 311° C.; GC Analysis Result >99.27%.

Example 6

Synthesis of Tris-Diethylaminodimethylsilyl Amine 180 g (0.65 mol) of diethylamino dimethyl disilazane (($CH_3$)$_2$SiN($CH_2CH_3$)$_2$)$_2$NH) synthesized by Example 1 above and 200 ml of n-hexane organic solvent were added to 2000 mL of a flame-dried flask under anhydrous and inert atmosphere while stirring, and 202.16 g (0.65 mol) of 2.29M normal butyl lithium (n-$C_4H_9$Li).hexane ($C_6H_{14}$) solution was slowly added while maintaining a temperature of −15° C. After the addition was completed, a temperature of the reaction solution was slowly raised to room temperature, and the reaction solution was stirred for 12 hours and 200 ml of tetrahydrofuran (O($C_2H_2$)$_2$) was added thereto. 84.30 g (0.65 mol) of dichloro dimethylsilane was slowly added to the reaction solution while maintaining a temperature of −20° C. After the addition was completed, a temperature of the reaction solution was slowly raised to 65° C. and the reaction solution was stirred for 12 hours while maintaining the temperature. After the white solid obtained by filtration of the reaction mixture was removed to obtain a filtrate, 51.65 g (0.65 mol) of lithium diethylamine salt (LiN($C_2H_5$)$_2$) obtained by reacting diethylamine (HN($C_2H_5$)$_2$) with 2.29M normal butyl lithium (n-$C_4H_9$Li).hexane ($C_6H_{14}$) solution in a quantitative scheme was slowly added thereto while stirring the filtrate and maintaining a temperature of −20° C. After the addition was completed, a temperature of the reaction solution was slowly raised to 65° C. and the reaction solution was stirred for 12 hours while maintaining the temperature. After the white solid obtained by filtration of the reaction mixture was removed to obtain a filtrate, solvent was removed from the filtrate under reduced pressure, and 171.88 g (0.42 mol) of tris-diethylaminosilyl amine (N(Si(CH$_3$)$_2$N(CH$_2$CH$_3$)$_2$)$_3$) was obtained by reduced pressure distillation with a yield of 65%.

$^1$H NMR (inC$_6$D$_6$) δ 0.37 (s, 18H, NSi(CH$_3$)$_2$N), 1.02 (t, 18H, Si(NCH$_2$CH$_3$)$_2$), 2.86 (q, 12H, Si(NCH$_2$CH$_3$)$_2$); Boiling Point 311° C.; GC Analysis Result >99.27%.

Example 7

Synthesis of Dimethylamino Methyl Disilazane 250 g (1.55 mol) of hexamethyl disilazane (((CH$_3$)$_3$Si)$_2$NH) and 10 g (0.075 mol) of aluminum chloride (AlCl$_3$) were put into 2000 mL of a flame-dried Schlenk flask under anhydrous and inert atmosphere while stirring, 713.19 g (6.20 mol) of dichloro methylsilane (CH$_3$SiHCl$_2$) was slowly added thereto while maintaining temperature of 25° C., and a temperature of the reaction solution was slowly raised to 40° C. The mixed reaction solution was stirred for 3 hours and the produced chlorotrimethylsilane ((CH$_3$)$_3$SiCl) and the excessively added dichloro methylsilane (CH$_3$SiHCl$_2$) were removed therefrom by simple distillation or distillation under reduced pressure. The recovered chloro methyl disilazane ((CH$_3$SiHCl)$_2$NH)) solution was stirred and then 293.47 g (4.2 mol) of dimethylamine ((CH$_3$)$_2$NH) was slowly added thereto while maintaining temperature of –15° C. After the addition was completed, a temperature of the reaction solution was slowly raised to room temperature, and the reaction solution was stirred at room temperature for 6 hours. The white solid obtained by filtration was removed to obtain a filtrate. Solvent was removed from the filtrate under reduced pressure, and 222.54 g (1.16 mol) of dimethylamino methyl disilazane ((CH$_3$SiHN(CH$_3$)$_2$)$_2$NH) was obtained by reduced pressure distillation with a yield of 75%.

$^1$H-NMR (inC$_6$D$_6$): δ 0.12 (s, 6H, ((CH$_3$)SHiN), 2.47 (s, 12H, (((CH$_3$)$_2$)$_2$NSi), 4.43 (m, 2H, ((CH$_3$)HSiNH).

Example 8

Synthesis of Bis-Dimethylaminomethylsilyl Trimethylsilyl Amine 191.43 g (1.00 mol) of dimethylamino methyl disilazane ((CH$_3$SiHN(CH$_3$)$_2$)$_2$NH) synthesized by Example 7 above and 200 ml of n-hexane organic solvent were added to 2000 mL of a flame-dried flask under anhydrous and inert atmosphere while stirring, and 303.32 g (1.00 mol) of 2.29M normal butyl lithium (n-C$_4$H$_9$Li).hexane (C$_6$H$_{14}$) solution was slowly added while maintaining a temperature of –15° C. After the addition was completed, a temperature of the reaction solution was slowly raised to room temperature, and the reaction solution was stirred for 12 hours and 300 ml of tetrahydrofuran (O(C$_2$H$_2$)$_2$) was added thereto. 108.64 g (1.00 mol) of chlorotrimethylsilane was slowly added to the reaction solution while maintaining a temperature of –20° C. After the addition was completed, a temperature of the reaction solution was slowly raised to 65° C. and the reaction solution was stirred for 12 hours while maintaining the temperature. After the reaction was completed, the white solid obtained by filtration of the reaction mixture was removed to obtain a filtrate, solvent was removed from the filtrate under reduced pressure, and 184.53 g (0.70 mol) of bis-dimethylaminomethylsilyl trimethylsilyl amine ((CH$_3$)$_3$SiN(SiH(CH$_3$)N(CH$_3$)$_2$)$_2$) was obtained by reduced pressure distillation with a yield of 70%.

$^1$H-NMR (inC$_6$D$_6$) δ 0.29 (m, 15H, NSiH(CH$_3$)N(CH$_3$)$_2$, NSi(CH$_3$)$_3$) 2.46 (m, 12H, NSiH(CH$_3$)N(CH$_3$)$_2$), 4.76 (m, 2H, NSiH(CH$_3$)N(CH$_3$)$_2$); Boiling Point 237° C.; GC Analysis Result >99.5%.

Example 9

Deposition of Silicon Oxide Film of Amino-Silyl Amine Compound by Plasma Enhanced Atomic Layer Deposition (PEALD)

Figure 8:
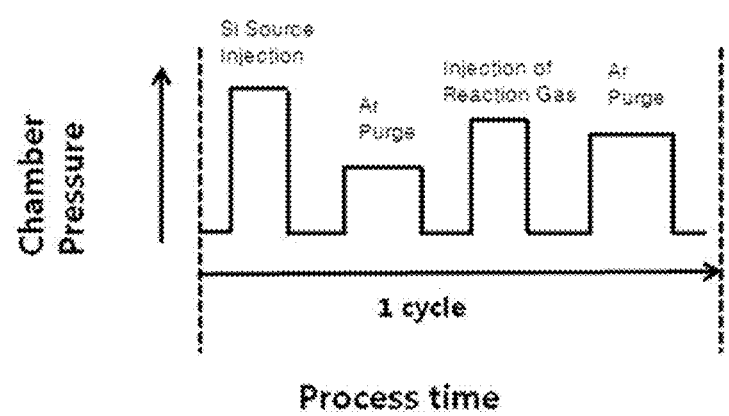
FIG. 8 shows a silicon-containing thin-film deposition method practiced by Examples 9 and 10.

Silicon oxide thin-films were manufactured with silicon-containing compositions for thin-film deposition containing the amino-silyl amine compounds according to Examples 3 to 6 and 8 of the present invention, respectively, under the same conditions as shown in the following Table 1, by plasma enhanced atomic layer deposition (PEALD) apparatus using the known PEALD method, and properties of the silicon oxide thin-films were evaluated. Oxygen together with plasma was used as the reaction gas, and argon being an inert gas was used as purge gas. Hereinafter, FIG. 8 and Table 1 specifically show a method for depositing the silicon oxide thin-film.

TABLE 1

| | Silicon Oxide Thin-Film Deposition Conditions | | | | | | | | | |
|---|---|---|---|---|---|---|---|---|---|---|
| | | | | | | 400 W Oxygen Plasma | | | | |
| | Heating Temperature of Precursor (° C.) | Temperature of Substrate (° C.) | Time (sec) Required for Injecting Precursor | Purge | | Flow Rate of Oxygen/ Argon (sccm) | Time (Sec) | Purge | | Number of Deposition Cycle |
| | | | | Flow Rate (sccm) | Time (Sec) | | | Flow Rate (sccm) | Time (Sec) | |
| Bis-Diethylamino Dimethylsilyl Trimethylsilyl Amine | 90 | 100 | 7 | 1100 | 20 | 300/100 | 10 | 1100 | 15 | 50 |
| Tris-Diethylamino Dimethylsilyl Amine | 90 | 100 | 9 | 1100 | 20 | 300/100 | 10 | 1100 | 15 | 50 |
| Bis- | 70 | 100 | 6 | 1100 | 20 | 300/100 | 10 | 1100 | 15 | 50 |

TABLE 1-continued

Silicon Oxide Thin-Film Deposition Conditions

| | Heating Temperature of Precursor (° C.) | Temperature of Substrate (° C.) | Time (sec) Required for Injecting Precursor | Purge Flow Rate (sccm) | Purge Time (Sec) | 400 W Oxygen Plasma Flow Rate of Oxygen/Argon (sccm) | Time (Sec) | Purge Flow Rate (sccm) | Purge Time (Sec) | Number of Deposition Cycle |
|---|---|---|---|---|---|---|---|---|---|---|
| Dimethylaminomethylsilyl Trimethylsilyl Amine | | | | | | | | | | |
| Bis-Dimethylaminomethylsilyl Trimethylsilyl Amine | 60 | 100 | 6 | 1100 | 20 | 300/100 | 10 | 1100 | 15 | 50 |

Figure 9:
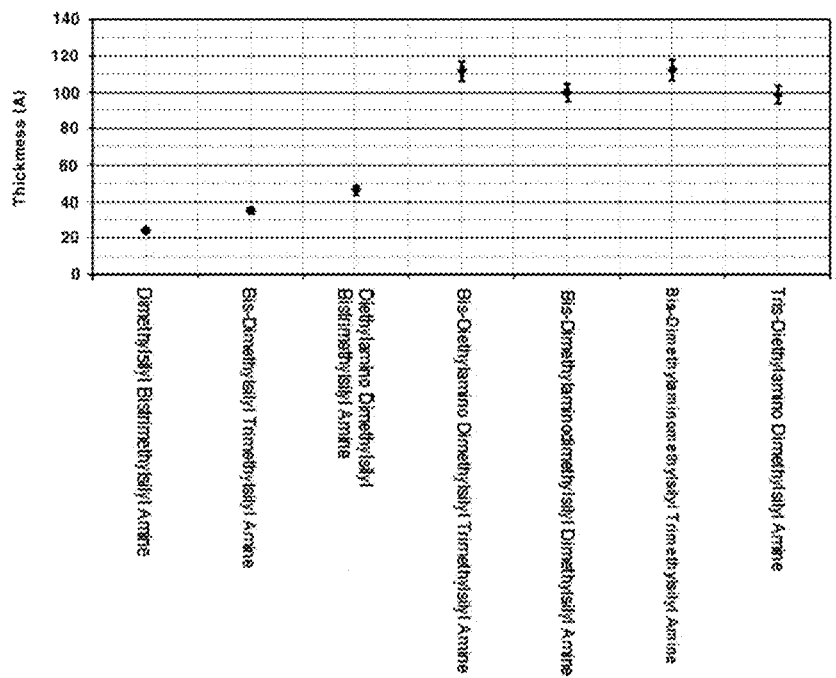
FIG. 9 shows each thickness of silicon-containing thin-films manufactured by Example 9 and Comparative Example through Ellipsometer analysis.
Figure 10:
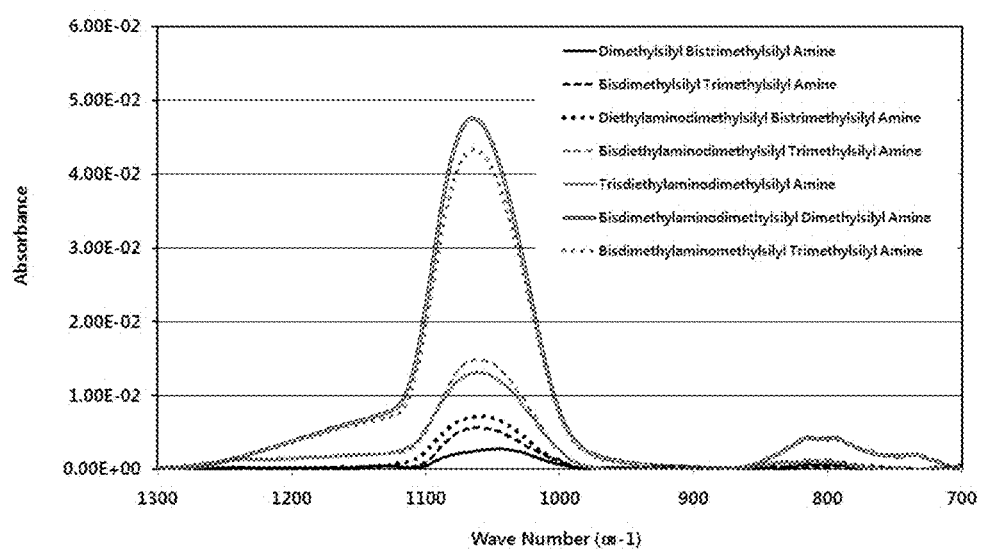
FIG. 10 shows Infrared Spectroscopy analysis of the deposited silicon-containing thin-film manufactured by Example 9.

Each thickness of deposited thin-films was measured by Ellipsometer, and formation of silicon oxide film was observed by infrared spectroscopy. FIG. 9 shows each thickness of the films observed by Ellipsometer. It was shown that the thicknesses of thin-films ranging 99 to 112.5 Å are different from each other depending on the kind or the number of substituents, and it is determined that the thin-film is useful in all silicon oxide thin-film application fields requiring high deposition rate. FIG. 10 shows infrared spectroscopy analysis of the deposited film. It was shown that all of the silicon oxide thin-films were formed, and peak of impurities such as C—H, Si—OH was not observed.

That is, it was confirmed that the novel amino-silyl amine compound prepared by the present invention has high value in forming a silicon oxide thin-film having high purity and high deposition rate by PEALD.

Comparative Example

Deposition of Silicon Oxide Film of Known Amino-Silyl Amine Compound by Plasma Enhanced Atomic Layer Deposition (PEALD)

Silicon oxide films were manufactured under the same deposition conditions as practiced by Example 9 above except for using known amino-silyl amine compounds as shown in the following Table 2, by known plasma enhanced atomic layer deposition (PEALD), and properties of the silicon oxide films were evaluated, and the deposited thin-films were analyzed by the same analysis method and conditions as practiced by Example 9 above and the analysis result thereof was obtained. Hereinafter, FIG. 8 and Table 2 specifically show a method for depositing the silicon oxide thin-film.

The thin-films had a thickness ranging 21 to 35.5 Å, which had a low deposition rate as compared to the amino-silyl amine of Examples 3 to 6 and 8, and it was shown that all of the silicon oxide thin-films were formed.

TABLE 2

Silicon Oxide Thin-Film Deposition Conditions

| | Heating Temperature of Precursor (° C.) | Temperature of Substrate (° C.) | Time (sec) Required for Injecting Precursor | Purge Flow Rate (sccm) | Purge Time (Sec) | 400 W Oxygen Plasma Rate of Oxygen/Argon (sccm) | Time (Sec) | Purge Flow Rate (sccm) | Purge Time (Sec) | Number of Deposition Cycle |
|---|---|---|---|---|---|---|---|---|---|---|
| Dimethylsilyl Bistrimethylsilyl Amine | 40 | 100 | 1 | 1100 | 20 | 300/100 | 10 | 1100 | 15 | 50 |
| Bis-Dimethylsilyl Trimethylsilyl Amine | 40 | 100 | 1 | 1100 | 20 | 300/100 | 10 | 1100 | 15 | 50 |
| Diethylamino Dimethylsilyl | 80 | 100 | 3 | 1100 | 20 | 300/100 | 10 | 1100 | 15 | 50 |

TABLE 2-continued

| | | | | | 400 W Oxygen Plasma | | | | |
|---|---|---|---|---|---|---|---|---|---|
| | | Time (sec) Required for Injecting Precursor | Purge | | Rate of Oxygen/ Argon (sccm) | Time (Sec) | Purge | | Number of Deposition Cycle |
| Heating Temperature of Precursor (° C.) | Temperature of Substrate (° C.) | | Flow Rate (sccm) | Time (Sec) | | | Flow Rate (sccm) | Time (Sec) | |
| Bistrimethylsilyl Amine | | | | | | | | | |

Example 10

Deposition of Silicon Nitride Film and Silicon Carbonitride Film of Amino-Silyl Amine Compound by Plasma Enhanced Atomic Layer Deposition (PEALD)

Silicon nitride film and silicon carbonitride films were manufactured with silicon-containing compositions for thin-film deposition containing the amino-silyl amine compounds according to Examples 3 to 6 and 8 of the present invention, respectively, by general plasma enhanced atomic layer deposition (PEALD) apparatus using the known PEALD method, and properties of the films were evaluated. Nitrogen ($N_2$), ammonia ($NH_3$), and argon (Ar) were used alone or in combination with one another as the reaction gas, and argon being an inert gas was used as purge gas. Hereinafter, FIG. 8 and Table 3 specifically show a method for depositing the silicon nitride film and silicon carbonitride film.

TABLE 3

Silicon Nitride and Silicon Carbonitride Thin-Film Deposition Conditions

| | Heating Temperature of Precursor (° C.) | Temperature of Substrate (° C.) | Time (sec) Required for Injecting Precursor | Purge | | 400 W $N_2/NH_3/Ar$ Plasma | | Purge | | Number of Deposition Cycle |
|---|---|---|---|---|---|---|---|---|---|---|
| | | | | Flow Rate (sccm) | Time (Sec) | $N_2/NH_3/Ar$ Flow Rate (sccm) | Time (Sec) | Flow Rate (sccm) | Time (Sec) | |
| Bis-Diethylamino Dimethylsilyl Trimethylsilyl Amine | 90 | 400 | 7 | 1100 | 20 | 150/30/0 | 10 | 1100 | 15 | 50 |
| Tris-diethylamino Dimethylsilyl Amine | 90 | 400 | 9 | 1100 | 20 | 150/30/0 | 10 | 1100 | 15 | 50 |
| Bis-Dimethylaminomethylsilyl Trimethylsilyl Amine | 60 | 300 | 15 | 1100 | 20 | 200/30/0 | 10 | 1100 | 15 | 600 |
| Bis-Dimethylaminomethylsilyl Trimethylsilyl Amine | 60 | 300 | 6 | 1100 | 20 | 60/10/0 | 10 | 1100 | 15 | 700 |
| Bis-Dimethylaminomethylsilyl Trimethylsilyl Amine | 60 | 300 | 6 | 1100 | 20 | 200/0/0 | 10 | 1100 | 15 | 600 |
| Bis-Dimethylaminomethylsilyl Trimethylsilyl Amine | 60 | 300 | 6 | 1100 | 20 | 50/0/30 | 10 | 1100 | 15 | 500 |
| Bis-Dimethylaminomethylsilyl Trimethylsilyl Amine | 60 | 300 | 6 | 1100 | 20 | 0/0/50 | 10 | 1100 | 15 | 700 |

Figure 11:
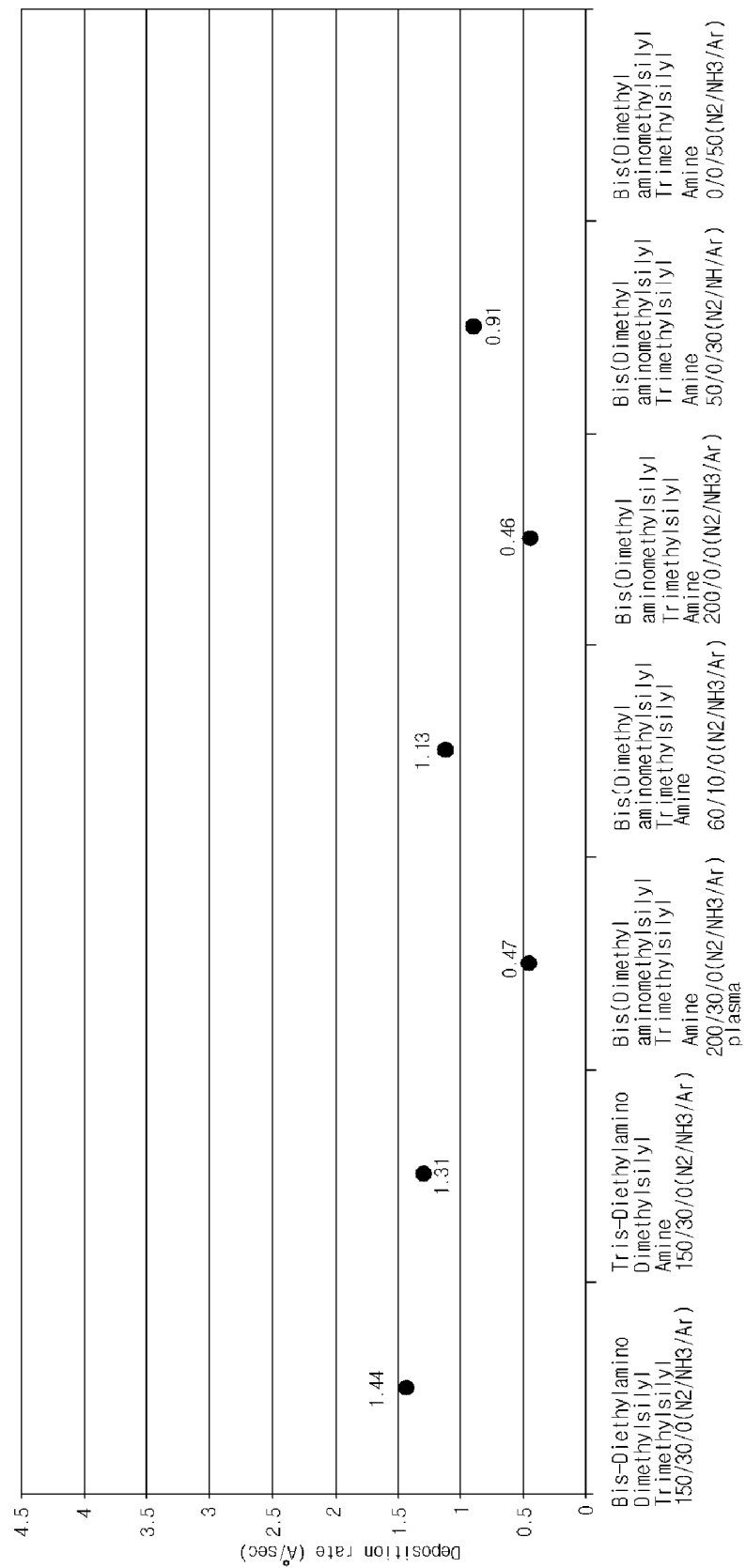
FIG. 11 shows a deposition rate of the silicon-containing thin-film manufactured by Example 10 through Ellipsometer and Transmission Electron Microscope (TEM)
Figure 13:
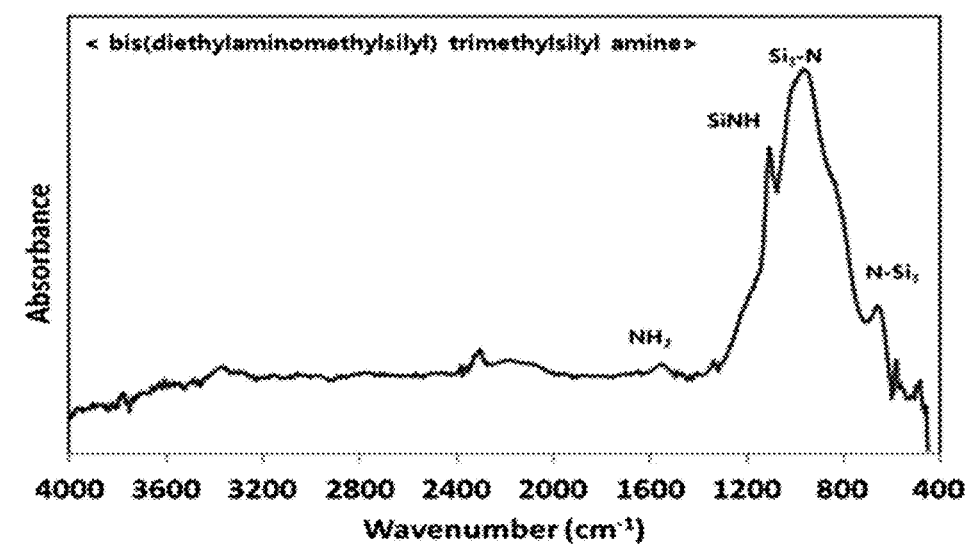
FIG. 13 shows Infrared Spectroscopy analysis of the deposited silicon-containing thin-film manufactured by Example 10.
Figure 13:
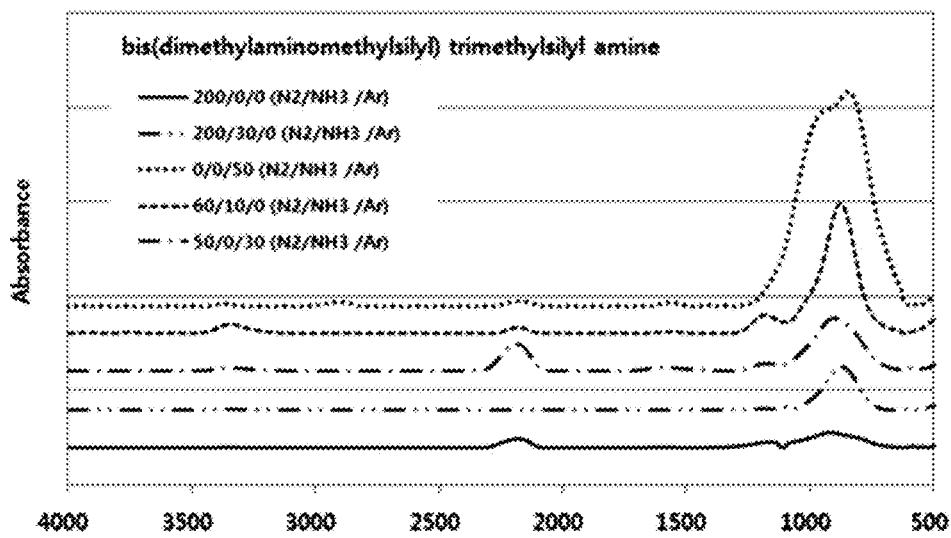
Figure 14:
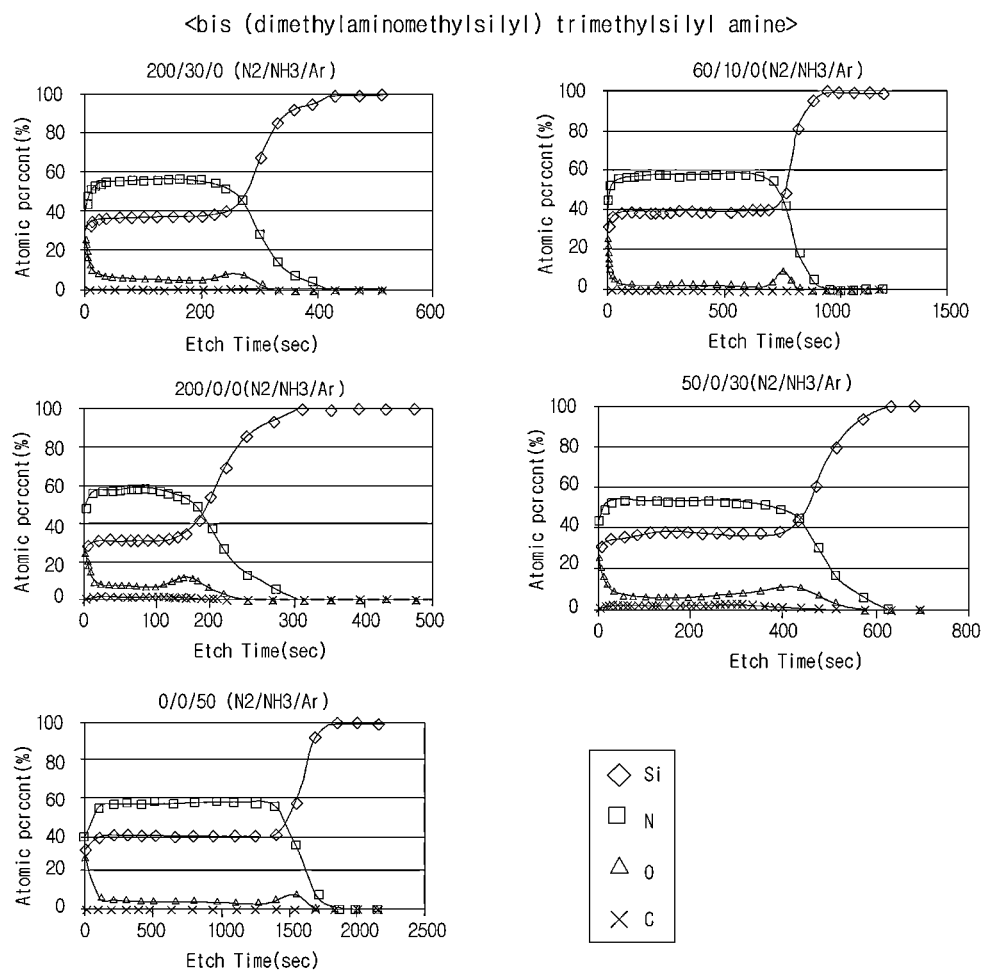
FIG. 14 shows a result obtained by analyzing composition of the deposited silicon-containing thin-film manufactured by Example 10 through Auger Electron Spectroscopy (AES)
Figure 15:
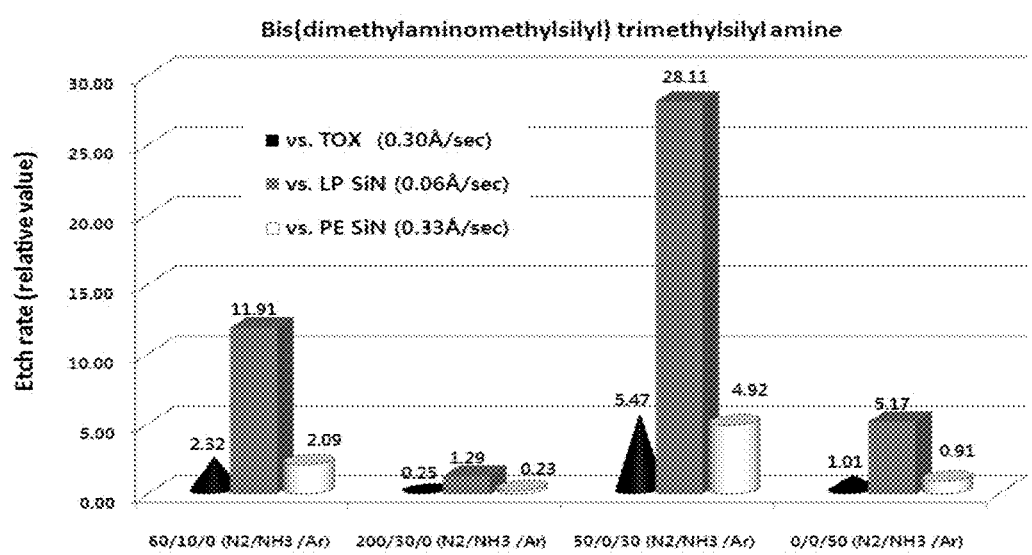
FIG. 15 shows a result obtained by analyzing resistance of the silicon-containing thin-film manufactured by Example 10 to hydrogen fluoride (300:1 BOE solution).

Each thickness of the deposited thin-films was measured by Ellipsometer and Transmission Electron Microscope (TEM) and formation of silicon nitride and silicon carbonitride films was observed by Infrared Spectroscopy (IR) and Auger Electron Spectroscopy (AES). FIG. 11 shows each deposition rate of thin-films observed by Ellipsometer and TEM. It was shown that the deposition rate of the thin-films ranging 0.43 to 4.25 Å are different from each other depending on the kind or the number of substituents and reaction gas, as shown in FIG. 11. FIG. 12 shows a result obtained by observing each thickness of the manufactured thin-films by TEM and verifying the deposition rate of the thin-films. FIGS. 13 and 14 show the analysis result of the deposited thin-films and the composition thereof by Infrared Spectroscopy and AES, respectively. It could be appreciated from FIGS. 13 and 14 that when mixing nitrogen ($N_2$) with ammonia ($NH_3$) to be used, the silicon nitride thin-film was formed, and when using nitrogen or argon alone or when mixing nitrogen with argon to be used, the silicon carbonitride thin-film containing 1.79 to 11.72% carbons was formed. FIG. 15 shows a comparison analysis result showing resistance to hydrogen fluoride (300:1 BOE solution) of the silicon nitride thin-film and silicon carbonitride thin-film according to Example 10 of the present invention, with the silicon oxide thin-film or silicon nitride thin-film manufactured by the existing metal organic chemical vapor deposition (MOCVD) at high temperature, low pressure chemical vapor deposition (LPCVD) and plasma enhanced chemical vapor deposition (PECVD) using plasma. It was confirmed from FIG. 15 that the silicon nitride thin-film and silicon carbonitride thin-film manufactured by Example 10 of the present invention had 0.25 to 2.53 times the etching rate of TOX (silicon oxide thin-film manufactured by MOCVD at high temperature, 5.17 to 28.11 times the etching rate of LP SiN (silicon nitride thin-film manufactured by LPCVD) and 0.23 to 4.92 times the etching rate of PE SiN (silicon nitride thin-film manufactured by PECVD), which was appreciated that resistance to hydrogen fluoride thereof was excellent as compared to the silicon nitride thin-film deposited by PEALD known in the art.

That is, it was confirmed that the novel amino-silyl amine compound prepared by the present invention has high value in forming a high purity silicon nitride thin-film and silicon carbonitride thin-film capable of being deposited at a low temperature by plasma enhanced atomic layer deposition and it is determined that the compound is useful throughout all silicon nitride thin-film application fields.

The amino-silyl amine compound of the present invention has excellent thermal stability and high reactivity, such that the silicon-containing thin-film manufactured by using the amino-silyl amine compound as a precursor may have high purity and significantly excellent physical and electrical properties.

In addition, the amino-silyl amine compound of the present invention may have high content of silicon and be maintained in a liquid state at room temperature and under atmospheric pressure to thereby be easily stored and handled and have high volatility to be rapidly and easily deposited, and it is possible to deposit a thin-film having excellent cohesion and step coverage.

Further, the silicon-containing thin-film manufactured by using the amino-silyl amine compound of the present invention as a precursor may have high purity and significantly excellent physical and electrical properties.

What is claimed is:

1. A silicon-containing composition for thin-film deposition comprising an amino-silyl amine compound represented by the following Chemical Formula 1:

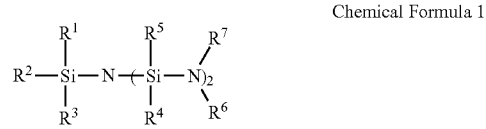

Chemical Formula 1 in Chemical Formula 1, $R^1$ to $R^5$ are each independently hydrogen, halogen, (C1-C7)alkyl, (C2-C7)alkenyl, (C2-C7)alkynyl, (C3-C7)cycloalkyl, or (C6-C12)aryl;

$R^6$ and $R^7$ are each independently hydrogen, (C1-C7)alkyl, (C2-C7)alkenyl, (C2-C7)alkynyl, (C3-C10)cycloalkyl, or (C6-C12)aryl, provided that a case where all $R^1$ to $R^7$ are methyl is excluded; and the alkyl, alkenyl, alkynyl, cycloalkyl, and aryl of $R^1$ to $R^5$, and the alkyl, alkenyl, alkynyl, cycloalkyl, and aryl of $R^6$ and $R^7$ may be further substituted with halogen, (C1-C7)alkyl, (C1-C7)alkoxy, or (C1-C7)aryloxy.

2. A method for manufacturing a silicon-containing thin-film using an amino-silyl amine compound represented by the following Chemical Formula 1:

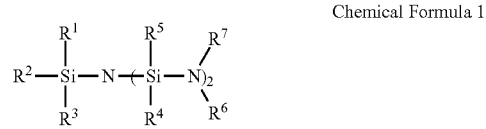

Chemical Formula 1 in Chemical Formula 1, $R^1$ to $R^5$ are each independently hydrogen, halogen, (C1-C7)alkyl, (C2-C7)alkenyl, (C2-C7)alkynyl, (C3-C7)cycloalkyl, or (C6-C12)aryl;

$R^6$ and $R^7$ are each independently hydrogen, (C1-C7)alkyl, (C2-C7)alkenyl, (C2-C7)alkynyl, (C3-C10)cycloalkyl, or (C6-C12)aryl, provided that a case where all $R^1$ to $R^7$ are methyl is excluded; and the alkyl, alkenyl, alkynyl, cycloalkyl, and aryl of $R^1$ to $R^5$, and the alkyl, alkenyl, alkynyl, cycloalkyl, and aryl of $R^6$ and $R^7$ may be further substituted with halogen, (C1-C7)alkyl, (C1-C7)alkoxy, or (C1-C7)aryloxy, wherein the manufacturing method is selected from the group consisting of metal organic chemical vapor deposition (MOCVD), atomic layer deposition (ALD), low pressure chemical vapor deposition (LPCVD), plasma enhanced chemical vapor deposition (PECVD), and plasma enhanced atomic layer deposition (PEALD).

3. A silicon-containing thin-film manufactured by using an amino-silyl amine compound represented by the following Chemical Formula 1:

Chemical Formula 1

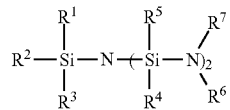

in Chemical Formula 1, $R^1$ to $R^5$ are each independently hydrogen, halogen, (C1-C7)alkyl, (C2-C7)alkenyl, (C2-C7)alkynyl, (C3-C7)cycloalkyl, or (C6-C12)aryl;

$R^6$ and $R^7$ are each independently hydrogen, (C1-C7)alkyl, (C2-C7)alkenyl, (C2-C7)alkynyl, (C3-C10)cycloalkyl, or (C6-C12)aryl, provided that a case where all $R^1$ to $R^7$ are methyl is excluded; and the alkyl, alkenyl, alkynyl, cycloalkyl, and aryl of $R^1$ to $R^5$, and the alkyl, alkenyl, alkynyl, cycloalkyl, and aryl of $R^6$ and $R^7$ may be further substituted with halogen, (C1-C7)alkyl, (C1-C7)alkoxy, or (C1-C7)aryloxy.

* * * * *